(12) United States Patent
Chen

(10) Patent No.: US 11,986,306 B2
(45) Date of Patent: May 21, 2024

(54) DIRECT SAMPLING ELECTRODE-TISSUE IMPEDANCE SYSTEM AND ASSOCIATED SIGNAL PROCESSING METHOD

(71) Applicant: MEDIATEK INC., Hsin-Chu (TW)

(72) Inventor: Chih-Hsin Chen, Hsinchu (TW)

(73) Assignee: MEDIATEK INC., Hsin-Chu (TW)

( * ) Notice: Subject to any disclaimer, the term of this patent is extended or adjusted under 35 U.S.C. 154(b) by 184 days.

(21) Appl. No.: 17/367,409

(22) Filed: Jul. 4, 2021

(65) Prior Publication Data

US 2022/0071543 A1 Mar. 10, 2022

Related U.S. Application Data

(60) Provisional application No. 63/145,553, filed on Feb. 4, 2021, provisional application No. 63/075,851, filed on Sep. 9, 2020.

(51) Int. Cl.
*A61B 5/308* (2021.01)
*A61B 5/00* (2006.01)
(Continued)

(52) U.S. Cl.
CPC ............ *A61B 5/308* (2021.01); *A61B 5/0531* (2013.01); *A61B 5/28* (2021.01); *A61B 5/318* (2021.01); *A61B 5/721* (2013.01); *A61B 2560/02* (2013.01)

(58) Field of Classification Search
CPC ......... A61B 5/308; A61B 5/0531; A61B 5/28; A61B 5/318; A61B 5/721
See application file for complete search history.

(56) References Cited

U.S. PATENT DOCUMENTS

2007/0002961 A1* 1/2007 Hoctor ................. A61B 5/0006 375/267
2013/0116577 A1* 5/2013 Yazicioglu .......... H01L 27/0811 600/483
(Continued)

FOREIGN PATENT DOCUMENTS

CN 209499724 U * 10/2019
EP 2 298 164 A2 3/2011
(Continued)

OTHER PUBLICATIONS

Motion Artifact in Biopotential Recordings, by Dilpreet Buxi et al., IEEE Sensors Journal, vol. 12, No. 12, Dec. 2012, pp. 3373-3383 (Year: 2012).*
(Continued)

*Primary Examiner* — Yingchuan Zhang
*Assistant Examiner* — Laura Hodge
(74) *Attorney, Agent, or Firm* — Winston Hsu

(57) ABSTRACT

The present invention provides a circuitry of a biopotential acquisition system comprising an input node, an ETI transmitter and an ADC. The input node is coupled to an electrode of the biopotential acquisition system, and the electrode is used to be in contact with a human body. The ETI transmitter is configured to generate a transmitter signal to the input node. The ADC is coupled to the input node, and is configured to process an input signal from the input node to generate a digital signal, wherein each of the input signal and the digital signal comprises components of an ECG signal and an ETI signal.

10 Claims, 3 Drawing Sheets

(51) Int. Cl.
*A61B 5/0531* (2021.01)
*A61B 5/28* (2021.01)
*A61B 5/318* (2021.01)

(56) References Cited

U.S. PATENT DOCUMENTS

| | | | | |
|---|---|---|---|---|
| 2015/0216481 A1* | 8/2015 | Kim | ....................... | A61B 5/316 |
| | | | | 600/509 |
| 2017/0354345 A1* | 12/2017 | Biancolillo | .......... | A61B 5/0535 |
| 2018/0168458 A1* | 6/2018 | Pekander | ............ | A61B 5/0809 |
| 2020/0077955 A1 | 3/2020 | Shui | | |

FOREIGN PATENT DOCUMENTS

| | | | | |
|---|---|---|---|---|
| EP | 2 298 164 A3 | 12/2011 | | |
| EP | 3669775 A1 * | 6/2020 | ............. | A61B 5/053 |

OTHER PUBLICATIONS

Sunyoung Kim, "A 2.4uA Continuous-time Electrode-Skin Impedance Measurement Circuit For Motion Artifact Monitoring in ECG Acquisition Systems", 2010 Symposium on VLSI Circuits/Technical Digest of Technical Papers, 2010.
Nick Van Helleputte, "A 160uA Biopotential Acquisition IC With Fully Integrated IA and Motion Artifact Suppression", IEEE Transactions on Biomedical Circuits and Systems, vol. 6, No. 6, Dec. 2012.
Nick Van Helleputte, "A Multi-Parameter Signal-Acquisition SoC for Connected Personal Health Applications", 2014 IEEE International Solid-State Circuits Conference, 2014.

* cited by examiner

DIRECT SAMPLING ELECTRODE-TISSUE IMPEDANCE SYSTEM AND ASSOCIATED SIGNAL PROCESSING METHOD

CROSS REFERENCE TO RELATED APPLICATIONS

This application claims the priority of U.S. Provisional Application No. 63/075,851 (filed on Sep. 9, 2020) and U.S. Provisional Application No. 63/145,553 (filed on Feb. 4, 2021), which is included herein by reference in its entirety.

BACKGROUND

A conventional medical device generally uses large dry electrodes or wet electrodes to measure physiological signals to obtain physiological features such as bio-impedance or electrocardiography. Recently, personal biosensors such as portable/wearable medical devices become popular for providing physiological information at all time for the reference to the user. Considering the use and design of these portable medical devices, smaller dry electrodes are more appropriate. However, smaller dry electrode means worse electrode impedance, and the worse electrode impedance (i.e. large electrode impedance) may cause detection error of electrocardiography (ECG) signals. In addition, because an electrode-tissue impedance (ETI) may change greatly due to contact factors or motion artifact, it increases the difficulty of measuring ECG signals.

To solve the problem of the ECG signals in the dry electrode application, the ETI is also detected to reduce the motion artifact in the ECG signals. In the conventional art, a current for the ETI measurement is injected into the electrodes, and an ETI receiver detects the voltages at the electrodes to determine the ETI. In detail, the ETI receiver may comprise a mixer, a low-pass filter and an analog-to-digital converter (ADC), and signals from the electrodes are processed by the mixer, the low-pass filter and the ADC in sequence to generate the ETI information. However, because the ETI receiver is an analog circuit, the ETI receiver has large chip area, higher power consumption and poor mixer harmonics, and the ETI receiver is not friendly to process scaling.

SUMMARY

It is therefore an objective of the present invention to provide a direct sampling ETI system, which uses only one analog front-end circuit to sense the ECG signal and ETI signal simultaneously, to solve the above-mentioned problems.

According to one embodiment of the present invention, a circuitry of a biopotential acquisition system comprising an input node, an ETI transmitter and an ADC is disclosed. The input node is coupled to an electrode of the biopotential acquisition system, and the electrode is used to be in contact with a human body. The ETI transmitter is configured to generate a transmitter signal to the input node. The ADC is coupled to the input node, and is configured to process an input signal from the input node to generate a digital signal, wherein each of the input signal and the digital signal comprises components of an ECG signal and an ETI signal.

According to another embodiment of the present invention, a signal processing method of a biopotential acquisition system comprises the steps of: generating a transmitter signal to an input node for an ETI measurement, wherein the input node is coupled to an electrode of the biopotential acquisition system, and the electrode is used to be in contact with a human body; and using an analog front-end circuit to process an input signal from an input node to generate a digital signal, wherein each of the input signal and the digital signal comprises components of an ECG signal and an ETI signal.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the following description and claims to refer to particular system components. As one skilled in the art will appreciate, manufacturers may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". The terms "couple" and "couples" are intended to mean either an indirect or a direct electrical connection. Thus, if a first device couples to a second device, that connection may be through a direct electrical connection, or through an indirect electrical connection via other devices and connections.

Figure 1:
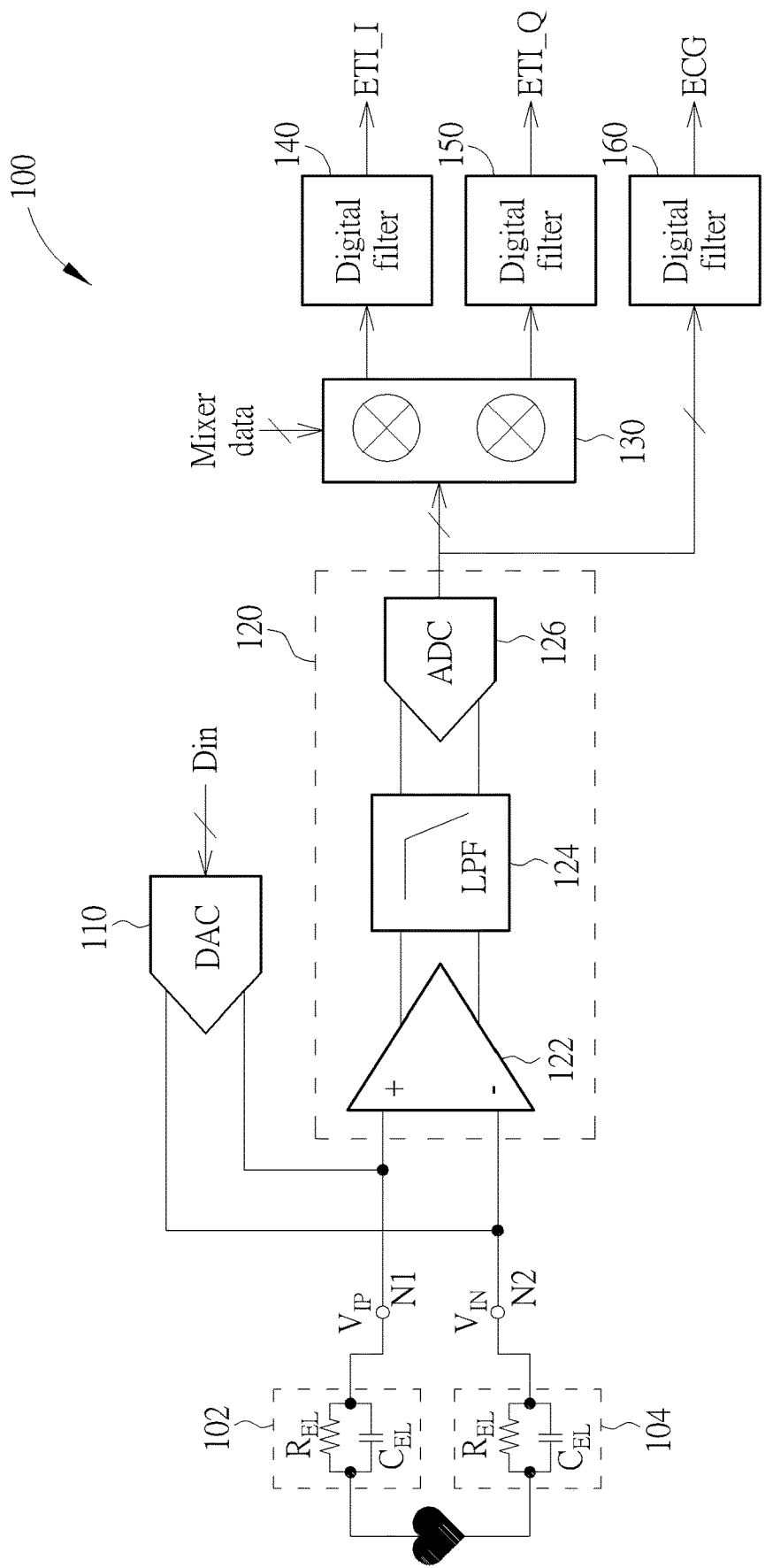
FIG. 1 is a diagram illustrating a biopotential acquisition system according to one embodiment of the present invention.

FIG. 1 is a diagram illustrating a biopotential acquisition system 100 according to one embodiment of the present invention. As shown in FIG. 1, the biopotential acquisition system 100 is a two-electrode biopotential acquisition system having two electrodes 102 and 104, and the electrodes 102 and 104 are used to connect to a right body (e.g., right hand) and a left body (e.g., left hand), respectively, to obtain biopotential signals of a human body, and the biopotential acquisition system 100 can process and analyze the biopotential signals to determine physiological signals such as ECG signals, and the physiological features can be displayed on a screen of the biopotential acquisition system 100. In this embodiment, the biopotential acquisition system 100 can be built in any portable electronic device or a wearable electronic device.

The biopotential acquisition system 100 comprises input nodes N1 and N2, an ETI transmitter (in this embodiment, a digital-to-analog converter (DAC) 110 serves as the ETI transmitter), an analog front-end circuit 120, a digital mixer 130 and digital filters 140, 150 and 160, wherein the analog front-end circuit 120 comprises a low-noise amplifier 122, a low-pass filter 124 and an ADC 126; and the DAC 110 can be implemented by any suitable DAC such as a current DAC, a capacitor DAC or a resistor DAC. When the electrodes 102 and 104 are connected to the human body, the ETI is formed so that the biopotential acquisition system 100 may have large input impedance, and the input impedance may change greatly due to contact factors or motion artifact. In the embodiment shown in FIG. 1, the ETI with the impedance of the electrode 102/104 are modeled as a resistor $R_{EL}$ and a capacitor $C_{EL}$ connected in parallel. In the operation of the biopotential acquisition system 100, when the electrodes 102 and 104 are in contact with the human body and the biopotential acquisition system 100 starts to measure the ECG signals, the DAC 110 receives a digital input signal Din to generate a transmitter signal to the electrodes 102 and 104. Then, the analog front-end circuit 120 receives the input signals $V_{IP}$ and $V_{IN}$ (biopotential signals) from the input nodes N1 and N2 that are respectively coupled to the electrodes 102 and 104 to generate information comprising the ECG signal and ETI signal. In detail, the low-noise amplifier 122 starts to receive input signals $V_{IP}$ and $V_{IN}$ (biopotential signals) from the input nodes N1 and N2 to generate amplified signals, wherein the input signals $V_{IP}$ and $V_{IN}$ comprise information/components of the ECG signal and ETI signal. Then, the low-pass filter 124 filters the amplified signals to generate filtered signals. In one embodiment, a frequency of the transmitter signal generated by the DAC 110 is higher than the ECG signals, for example, the ECG signals may have frequency lower than several hundred hertz, but the transmitter signal generated by the DAC 110 may be several kilohertz, therefore, the low-pass filter 124 may filter out components above several kilohertz and retain the components of the ECG signal and ETI signal within the amplified signal. Then, the ADC 126 performs an analog-to-digital converting operation on the filtered signal to generate a digital signal.

The digital mixer 130 has an in-phase path and a quadrature path, and a mixer within the in-phase path mixes an in-phase signal of the digital signal with mixer data whose phase is in-phase with the digital signal to generate an in-phase mixed signal, and a mixer within the quadrature path mixes a quadrature signal of the digital signal with mixer data whose phase is in quadrature with the digital signal to generate a quadrature mixed signal. In this embodiment, a frequency of the mixer data is close to the frequency of the transmitter signal, so that the in-phase mixed signal and the quadrature mixed signal have lower frequency. In addition, the digital mixer 130 may be a multi-bit digital mixer having good harmonics.

In addition, the phase lead and lag of the signal communication and processing from the DAC 110 to an input of the digital mixer 130 can be compensated by internal phase shift compensation at the analog front-end circuit 120 and the digital mixer 130 to derive practical in-phase mixed signal and quadrature mixed signal.

The digital filter 140 filters the in-phase mixed signal generated by the digital mixer 130 to output an in-phase ETI signal ETU, and the digital filter 150 filters the quadrature mixed signal generated by the digital mixer 130 to output a quadrature ETI signal ETI_Q.

Meanwhile, because the ECG signals has lower frequency such as several hundred hertz, the digital filter 160 may directly receive the digital signal outputted by the ADC 126, that is the digital signal is not processed by any mixer, and the digital filter 160 filters out components above several hundred hertz to obtain the ECG signal.

Finally, a following processing circuit (not shown) within the biopotential acquisition system 100 can notify the user about the motion artifact issue or to adjust/compensate the ECG signal generated by the ECG receiver 120 by using the ETI signal.

In the above embodiment, because the ECG signal and the ETI signal are processed by the same analog front-end circuit 120 simultaneously, and the ECG signal and the ETI signal are converted to digital signal without first performing a mixing operation, the biopotential acquisition system 100 may have smaller chip area and lower power consumption. In addition, because the digital mixer 130 is used for the mixing operation of the digital signal, the mixer harmonics can be improved. Furthermore, using the digital filters 140, 150 and 160 in the biopotential acquisition system 100 can reduce the chip area and reduce data rate.

Figure 2:
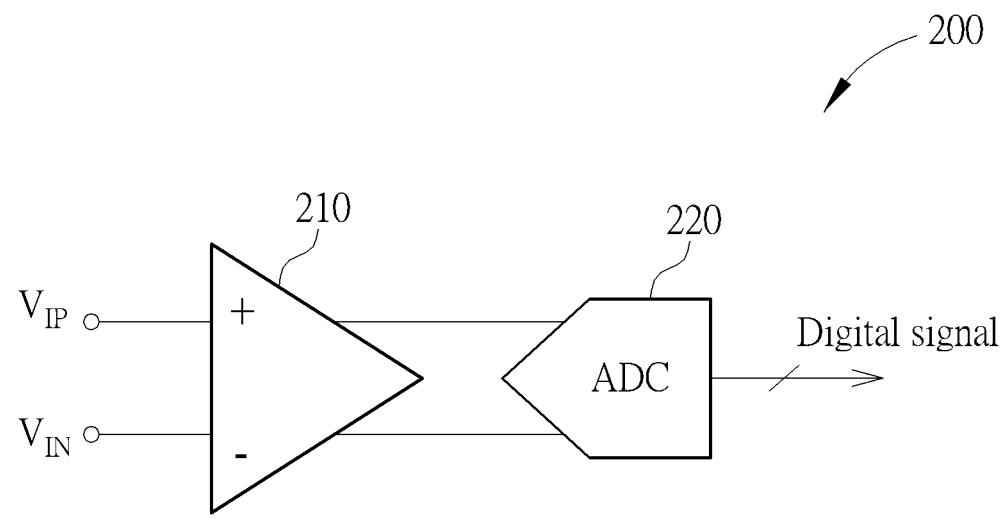
FIG. 2 is a diagram illustrating an analog front-end circuit according to one embodiment of the present invention.
Figure 3:
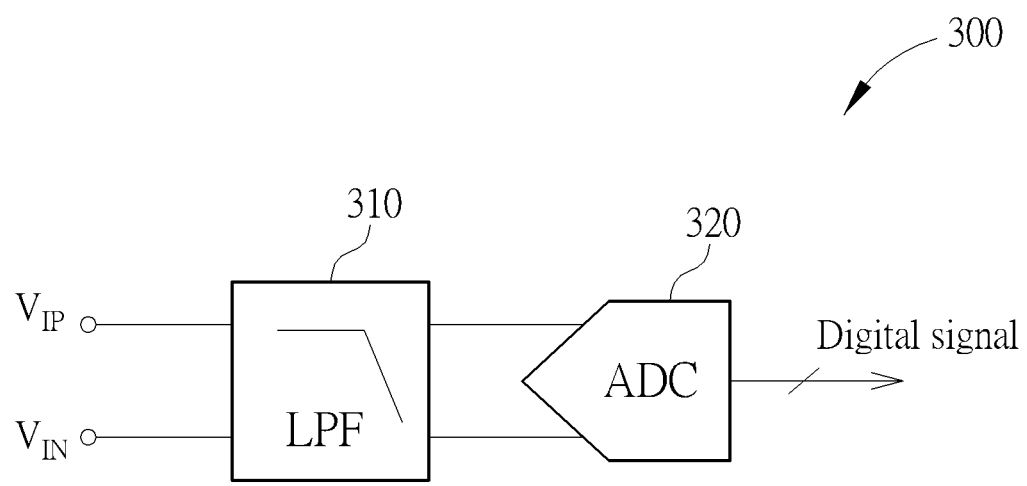
FIG. 3 is a diagram illustrating an analog front-end circuit according to another embodiment of the present invention.

In the embodiment shown in FIG. 1, the analog front-end circuit 120 comprises the low-noise amplifier 122, the low-pass filter 124 and the ADC 126, but this feature is not a limitation of the present invention. FIG. 2 is a diagram illustrating an analog front-end circuit 200 according to one embodiment of the present invention, wherein the analog front-end circuit 200 can be used to replace the analog front-end circuit 120 shown in FIG. 1. As shown in FIG. 2, the analog front-end circuit 200 comprises a low-noise amplifier 210 and an ADC 220, wherein the low-noise amplifier 210 is configured to receive input signals $V_{IP}$ and $V_{IN}$ (biopotential signals) from the electrodes 102 and 104 to generate an amplified signal, wherein the input signals $V_{IP}$ and $V_{IN}$ comprises information of the ECG signal and ETI signal; and the ADC 220 performs an analog-to-digital converting operation on the amplified signal to generate a digital signal. FIG. 3 is a diagram illustrating an analog front-end circuit 300 according to another embodiment of the present invention, wherein the analog front-end circuit 300 can be used to replace the analog front-end circuit 120 shown in FIG. 1. As shown in FIG. 3, the analog front-end circuit 300 comprises a low-pass filter 310 and an ADC 320, wherein the low-pass filter 310 filters the input signals $V_{IP}$ and $V_{IN}$ (biopotential signals) from the electrodes 102 and 104 to generate a filtered signal, for example, the low-pass filter 310 may filter out components above several kilohertz and retain the components of the ECG signal and ETI signal within the input signals $V_{IP}$ and $V_{IN}$; and the ADC 320 performs an analog-to-digital converting operation on the filtered signal to generate a digital signal.

Figure 4:
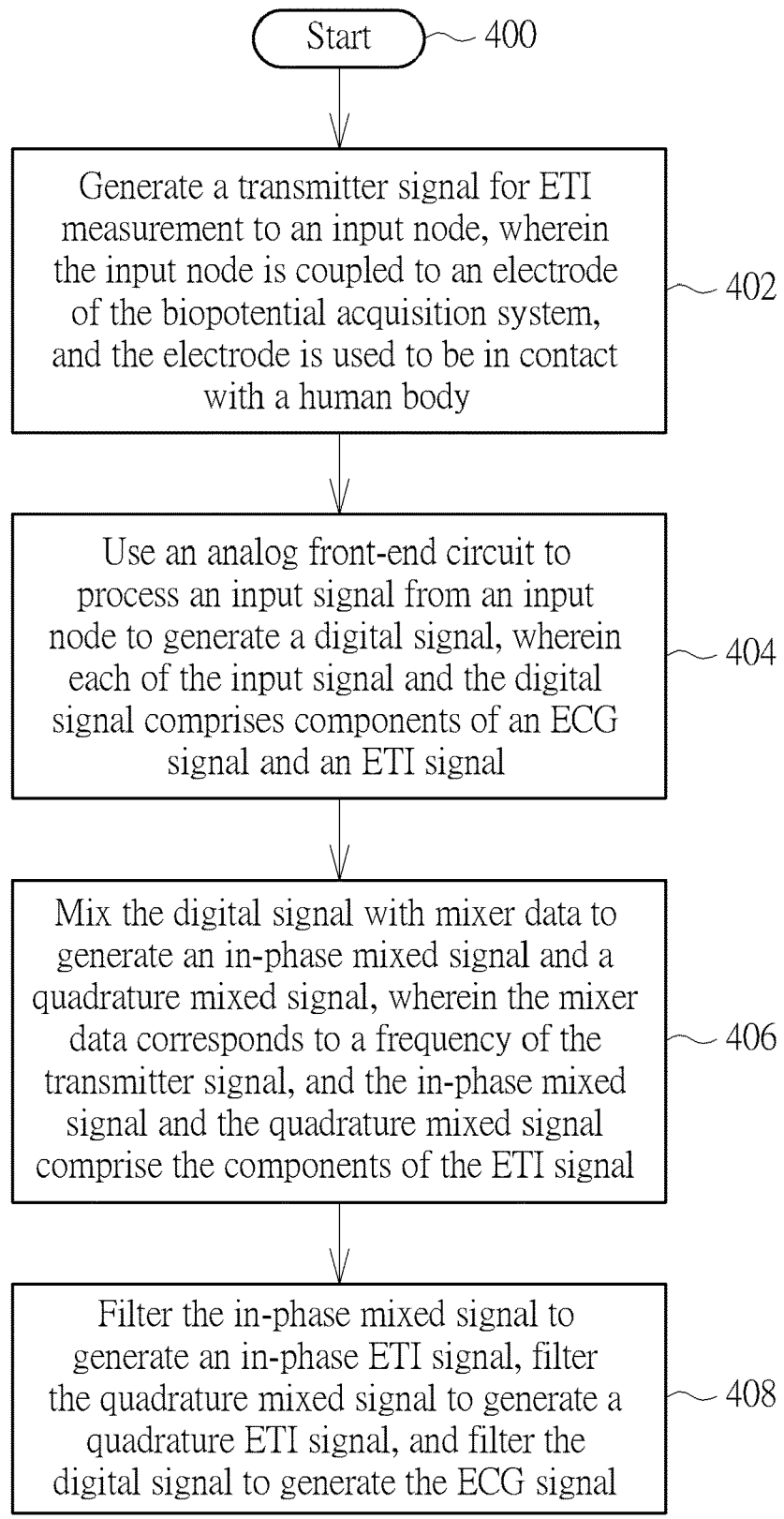
FIG. 4 is a flowchart of a signal processing method of the biopotential acquisition system according to one embodiment of the present invention.

FIG. 4 is a flowchart of a signal processing method of the biopotential acquisition system 100 according to one embodiment of the present invention. Referring to FIG. 1 and FIG. 4 together, the flowchart of the signal processing method is described as follows.

Step 400: the flow starts.

Step 402: generate a transmitter signal for ETI measurement to an input node, wherein the input node is coupled to an electrode of the biopotential acquisition system, and the electrode is used to be in contact with a human body.

Step 404: use an analog front-end circuit to process an input signal from an input node to generate a digital signal, wherein each of the input signal and the digital signal comprises components of an ECG signal and an ETI signal.

Step 406: mix the digital signal with mixer data to generate an in-phase mixed signal and a quadrature mixed signal, wherein the mixer data corresponds to a frequency of the transmitter signal, and the in-phase mixed signal and the quadrature mixed signal comprise the components of the ETI signal.

Step 408: filter the in-phase mixed signal to generate an in-phase ETI signal, filter the quadrature mixed signal to generate a quadrature ETI signal, and filter the digital signal to generate the ECG signal.

Briefly summarized, in the biopotential acquisition system of the present invention, only one analog front-end circuit is used to process two input signals to generate a digital signal comprising the components of the ECG signal and ETI signal, and the mixing operation and the filtering operation for obtaining the ETI signal are performed in digital domain. Therefore, the biopotential acquisition system has smaller chip are and lower power consumption.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A circuitry of a biopotential acquisition system, comprising:
   an input node, wherein the input node is coupled to an electrode of the biopotential acquisition system, and the electrode is configured to be in contact with a human body;
   an electrode-tissue impedance (ETI) transmitter, configured to generate a transmitter signal to the input node;
   an analog front-end circuit, coupled to the input node, configured to process an input signal from the input node to generate a digital signal, wherein each of the input signal and the digital signal comprises components of an electrocardiography (ECG) signal and an ETI signal;
   a digital filter, configured to filter the digital signal to generate the ECG signal; and
   a digital mixer, configured to mix the digital signal with mixer data to generate an in-phase mixed signal and a quadrature mixed signal, wherein the mixer data corresponds to a frequency of the transmitter signal, and the in-phase mixed signal and the quadrature mixed signal comprise the components of the ETI signal.

2. The circuitry of claim 1, wherein the analog front-end circuit comprise:
   an amplifier, wherein the amplifier amplifies the input signal to generate an amplified signal;
   a low-pass filter, coupled to the amplifier, configured to filter the amplified signal to generate a filtered signal; and
   an analog-to-digital converter (ADC), coupled to the low-pass filter, configured to perform an analog-to-digital converting operation on the filtered signal to generate the digital signal.

3. The circuitry of claim 1, wherein the analog front-end circuit comprise:
   an amplifier, wherein the amplifier amplifies the input signal to generate an amplified signal; and
   an ADC, coupled to the amplifier, configured to perform an analog-to-digital converting operation on the amplified signal to generate the digital signal.

4. The circuitry of claim 1, wherein the analog front-end circuit comprise:
   a low-pass filter, configured to filter the input signal to generate a filtered signal; and
   an ADC, coupled to the low-pass filter, configured to perform an analog-to-digital converting operation on the filtered signal to generate the digital signal.

5. A signal processing method of a biopotential acquisition system, comprising:
   generating a transmitter signal to an input node for an electrode-tissue impedance (ETI) measurement, wherein the input node is coupled to an electrode of the biopotential acquisition system, and the electrode is configured to be in contact with a human body;
   using an analog front-end circuit to process an input signal from an input node to generate a digital signal, wherein each of the input signal and the digital signal comprises components of an electrocardiography (ECG) signal and an ETI signal;
   mixing the digital signal with mixer data to generate an in-phase mixed signal and a quadrature mixed signal, wherein the mixer data corresponds to a frequency of the transmitter signal, and the in-phase mixed signal and the quadrature mixed signal comprise the components of the ETI signal; and
   filtering the digital signal to generate the ECG signal.

6. The signal processing method of claim 5, wherein the step of using the analog front-end circuit to process the input signal from the input node to generate the digital signal comprises:
   amplifying the input signal to generate an amplified signal;
   filtering the amplified signal to generate a filtered signal; and
   performing an analog-to-digital converting operation on the filtered signal to generate the digital signal.

7. The signal processing method of claim 5, wherein the step of using the analog front-end circuit to process the input signal from the input node to generate the digital signal comprises:
   amplifying the input signal to generate an amplified signal; and
   performing an analog-to-digital converting operation on the amplified signal to generate the digital signal.

8. The signal processing method of claim 5, wherein the step of using the analog front-end circuit to process the input signal from the input node to generate the digital signal comprises:
   filtering the input signal to generate a filtered signal; and
   performing an analog-to-digital converting operation on the filtered signal to generate the digital signal.

9. The signal processing method of claim 5, further comprising:
   filtering the in-phase mixed signal to generate an in-phase ETI signal; and
   filtering the quadrature mixed signal to generate a quadrature ETI signal.

10. The signal processing method of claim 9, further comprising:
    filtering the digital signal to generate the ECG signal.

* * * * *